United States Patent
Foley et al.

(10) Patent No.: US 6,248,107 B1
(45) Date of Patent: Jun. 19, 2001

(54) SYSTEM FOR REDUCING THE DISPLACEMENT OF A VERTEBRA

(75) Inventors: Kevin T. Foley, Germantown, TN (US); David L. Brumfield, Southaven, MS (US); Matthew M. Morrison, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/526,197

(22) Filed: Mar. 15, 2000

(51) Int. Cl.[7] .................................................. A61B 17/56
(52) U.S. Cl. .............................................................. 606/61
(58) Field of Search ................................... 606/60, 61, 72, 606/73

(56) References Cited

U.S. PATENT DOCUMENTS

| | | | |
|---|---|---|---|
| 4,175,555 | * 11/1979 | Herbert | 606/73 |
| 4,456,005 | * 6/1984 | Lichty | 606/60 |
| 4,611,581 | 9/1986 | Steffee . | |
| 4,696,290 | 9/1987 | Steffee . | |
| 4,854,311 | 8/1989 | Steffee . | |
| 5,254,118 | * 10/1993 | Mirkovic | 606/61 |
| 5,312,404 | 5/1994 | Asher et al. . | |
| 5,545,166 | * 8/1996 | Howland | 606/61 |
| 5,643,263 | 7/1997 | Simonson . | |
| 5,653,708 | 8/1997 | Howland . | |
| 5,782,831 | * 7/1998 | Sherman et al. | 606/61 |
| 5,885,285 | 3/1999 | Simonson . | |
| 6,123,707 | * 9/2000 | Wagner | 606/61 |

* cited by examiner

Primary Examiner—Gene Mancene
Assistant Examiner—Eduardo C. Robert
(74) Attorney, Agent, or Firm—Woodard, Emhardt, Naughton, Moriarty & McNett

(57) ABSTRACT

A method and an assembly for reducing a displaced vertebra and connecting the displaced vertebra to a spinal implant rod. The assembly has a reduction bolt with machine threads on one end and coarse threads on the other. A connection unit attaches the spinal rod to the reduction bolt, and until it is tightened, the connection unit allows the reduction bolt to slide within the connection unit. The connection unit includes a washer that rides against the side of the reduction bolt, and a nut is threaded onto the machine threads of the reduction bolt over a collar. The collar open is open at both ends and is of a size to readily slide over the reduction bolt. The posterior face of the collar has a notch to accept that portion of the lateral side of the washer as it presses against the reduction bolt. The notch is part of the open end of the collar into which is slide over the reduction bolt and down onto the connection unit. Arranged in this fashion, the nut can be tightened against the collar to move the displaced vertebra toward the longitudinal member. The third clamp can be tightened to secure the reduction bolt to the longitudinal member, and then the nut and the collar can be removed from the patient without the vertebra moving away from the longitudinal member.

24 Claims, 5 Drawing Sheets

SYSTEM FOR REDUCING THE DISPLACEMENT OF A VERTEBRA

This invention relates to orthopaedics and spinal surgery, and more particularly to a method and apparatus for reducing the extent of displacement between adjacent vertebrae.

BACKGROUND OF THE INVENTION

An apparatus for reducing the extent of displacement between adjacent vertebrae is shown in U.S. Pat. No. 4,611,581 to Steffee. That apparatus includes a pair of rigid plates, which are attached to opposite sides of the spinous process of the human spine. The plates are attached to the spine by bolts with coarse threads on one end and machine threads on the other. The coarse threads of the bolts are first screwed into the spine. The plates are then placed over the machine-threaded portion of the bolts, which are then held in place by nuts, threaded over the top of the plates. A displaced vertebra is relocated by pulling the vertebra toward the plate by tightening the nut on the bolt that holds the displaced vertebra.

A problem with this design is that it leaves a rather high profile of metal extending above the spine. The following invention is one solution to this problem.

SUMMARY

In one aspect, this invention is a reduction assembly for a spinal implant clamp that is used to connect a bone bolt to a spinal implant rod. The reduction assembly has a reduction bolt with machine threads on one end and coarse threads on the other end. A nut is then threaded on the machine threads over a collar. The collar open is open at both ends and is of a size to readily slide over the reduction bolt. The posterior face of the collar has a notch to accept a non-horizontal face on a spinal implant clamp and the nut and collar have mutually engageable male and female contacts that allow the nut to rotate in respect to the collar.

In another aspect, this invention is an assembly for reducing a displaced vertebra and connecting the displaced vertebra to a spinal implant rod. The assembly has a reduction bolt with machine threads on one end and coarse threads on the other. The assembly also has a connection unit to attach a spinal rod to the reduction bolt, and until it is tightened, the connection unit allows the reduction bolt to slide in the connection unit. The connection unit also includes a washer that rides against the side of the reduction bolt. A nut is threaded onto the machine threads of the reduction bolt over a collar. The collar is open at both ends and is of a size to readily slide over the reduction bolt. The posterior face of the collar has a notch to accept a portion of the lateral side of the washer as the washer presses against the reduction bolt. Hence, the notch is part of the open end of the collar into which one slides the collar over the reduction bolt and down onto the connection unit.

In another aspect, this invention is an apparatus for use in reducing a displaced vertebra. The apparatus has at least one longitudinal member positionable along the longitudinal axis of the spine, two vertebral anchors, three clamps and a reduction bolt. Two of the clamps fixedly secure each of the vertebral anchors to the longitudinal member. The third clamp is used to hold the reduction bolt to the longitudinal member, and when loose, allows a reduction bolt to slide within the clamp. The apparatus also includes a washer on the third clamp that rest against the side of the reduction bolt. A nut is threaded onto the machine threads of the reduction bolt over a collar. The collar is open at both ends and is of a size to readily slide over the reduction bolt. The posterior face of the collar has a notch to accept a portion of the lateral side of the washer as the washer presses against the reduction bolt. Hence, the notch is part of the open end of the collar into which one slides the collar over the reduction bolt and down onto the connection unit. Positioned in this fashion the nut can be tightened against the collar to pull the reduction bolt, previously threaded into a displaced vertebra, and thereby move the displaced vertebra toward the longitudinal member. The third clamp can be tightened to secure the reduction bolt to the longitudinal member, and then the nut and the collar can be removed from the patient without the vertebra moving away from the longitudinal member.

In yet another aspect, this invention is also a method for aligning a displaced vertebra. In general, the method includes the steps of attaching a bolt to a displaced vertebra; positioning a spinal rod along the longitudinal axis of the spine; positioning a clamping device on the bone bolt and the spinal rod, with clamping device having a compression member that, when engaged, simultaneously tightens the bone bolt and the spinal rod to the clamping device; sliding a collar over the bone bolt and allowing the collar to rest against the clamping device; threading a nut over the machine threads on the bone bolt and against the collar to move the displaced vertebra toward the spinal rod; tightening the compression member on the clamping device to hold the bone bolt and the spinal rod; and removing the nut and collar from the bone bolt.

An advantage of this invention is that it allows the nut that is typically used to hold a longitudinal member to a longitudinal member to be removed after a displaced vertebra has been relocated to its proper position by the surgeon.

DESCRIPTION OF PREFERRED EMBODIMENTS

Figure 1:
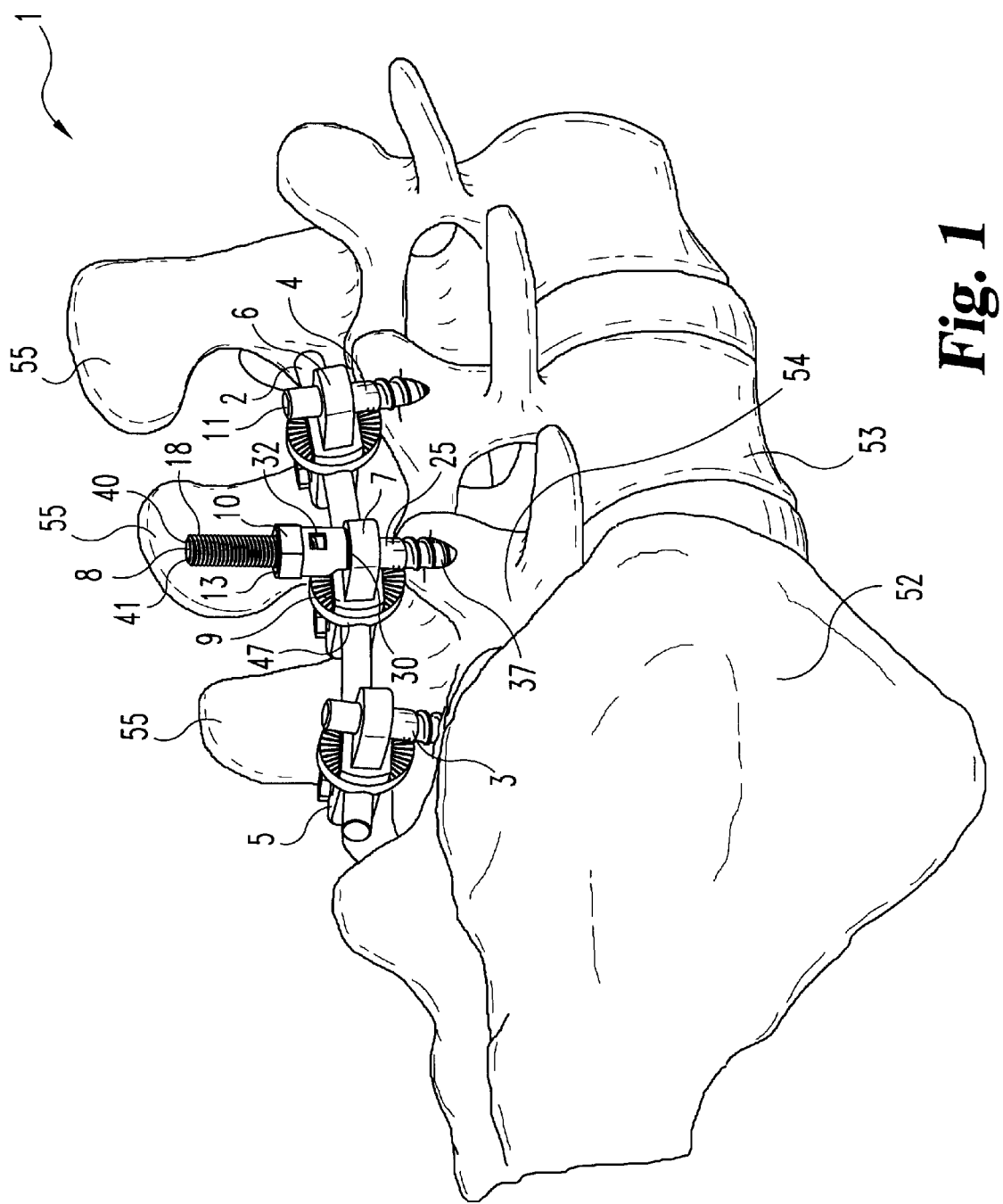
FIG. 1 is a perspective view of the application of the reduction apparatus according to one embodiment of the present invention.

For the purpose of promoting an understanding of the principles of the invention, reference will now be made to the embodiments illustrated in the drawings and specific language will be used to describe the same. It will nevertheless be understood that no limitations of the scope of the invention is thereby intended, and that such alterations and further modifications in the illustrated device, and that such further applications of the principles of the invention as illustrated therein are also contemplated as would normally occur to one skilled in the art to which the invention relates.

Figure 2:
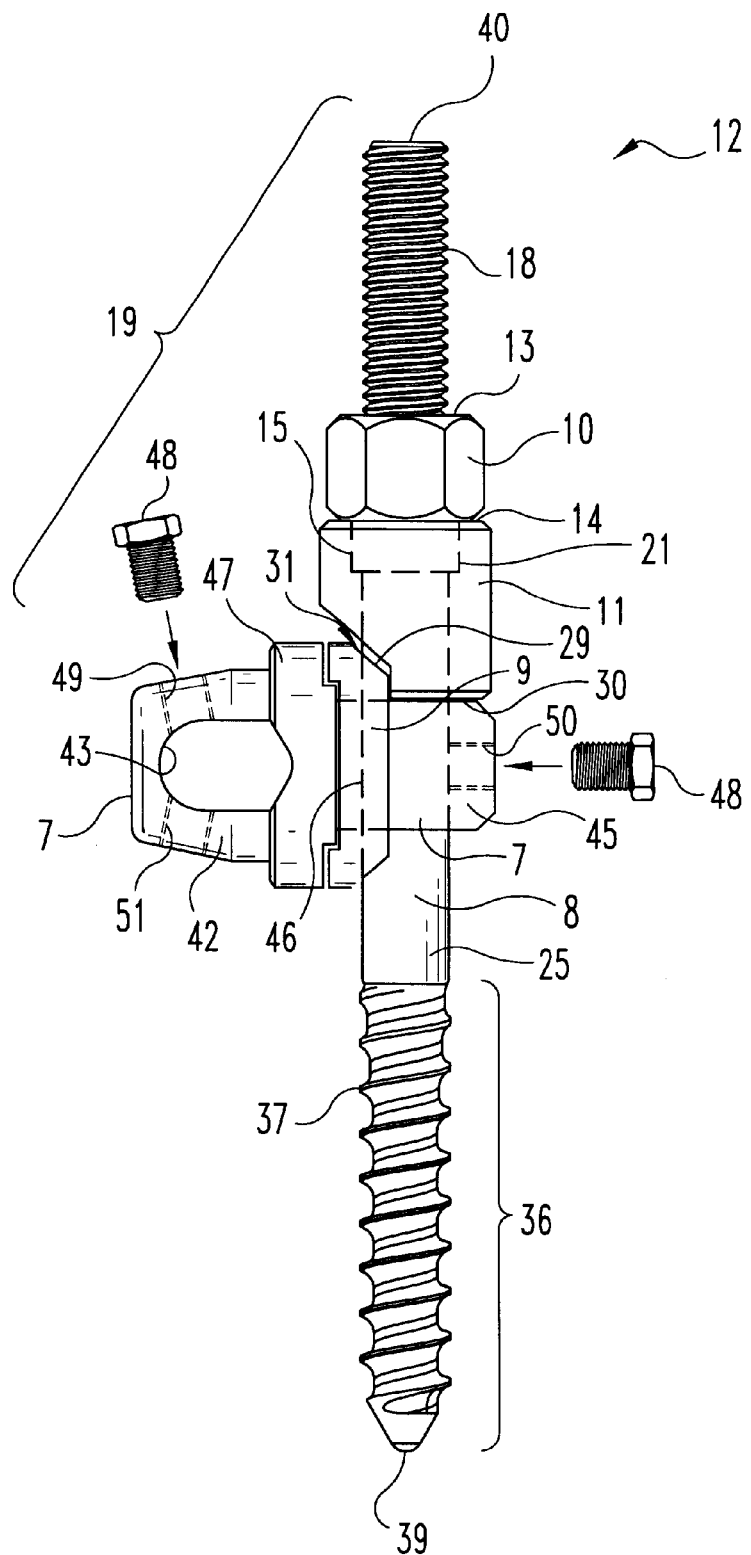
FIG. 2 is side elevational view of the reduction apparatus according to one embodiment of the present invention.

Referring to FIG. 1, there is shown an apparatus 1 for use in reducing a displaced vertebra 54. In this particular embodiment, apparatus includes a longitudinal member 2, two vertebral anchors 3 & 4, three rod-bolt clamps 5, 6 & 7, a reduction bolt 8, a bolt interface washer 9, a nut 10, and a clamp interface collar 11. The next figure, FIG. 2, depicts the reduction assembly 12 resting loosely in the third clamp or connection unit 7, and is shown removed from vertebra 52, 53 & 54 and removed from longitudinal member 2.

Figure 3:
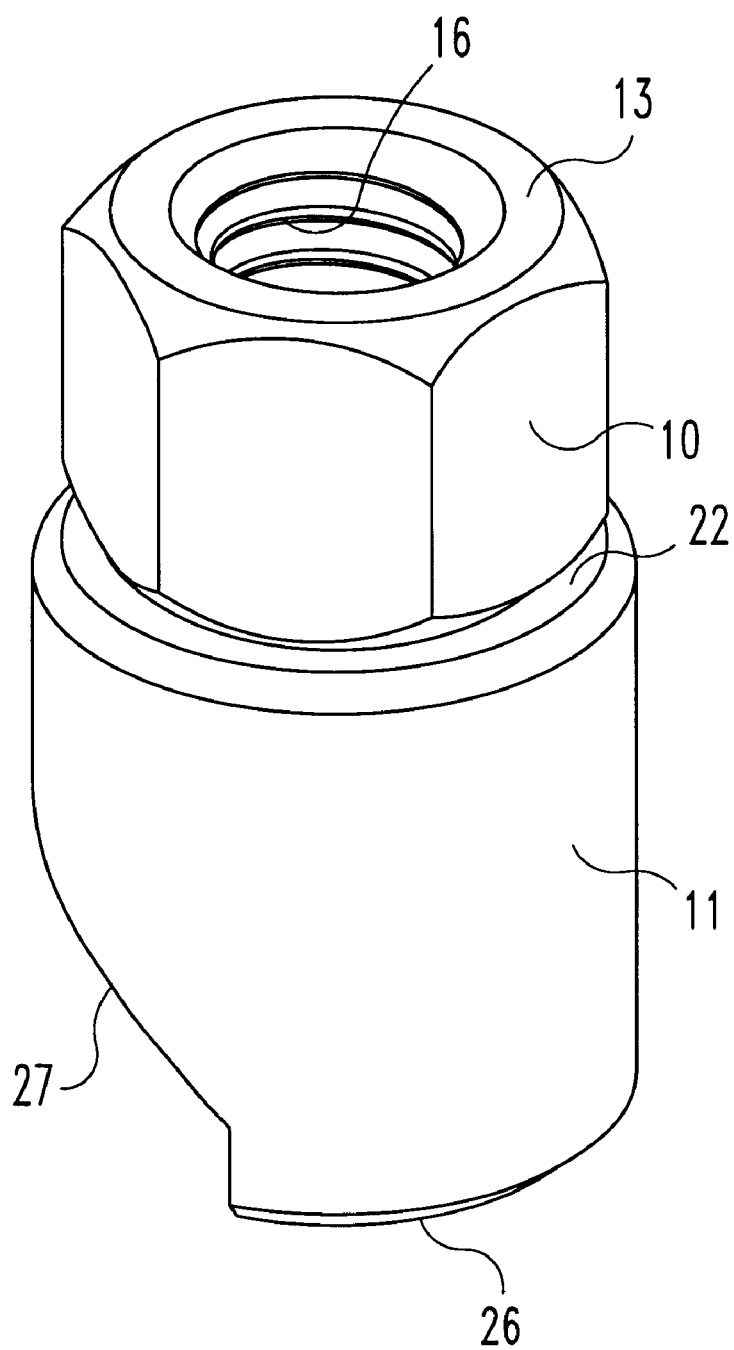
FIGS. 3, 4 and 5 are respectively perspective, side cross-sectional, and exploded side cross-sectional views of the nut and clamp interface collar according to one embodiment of the present invention.
Figure 4:
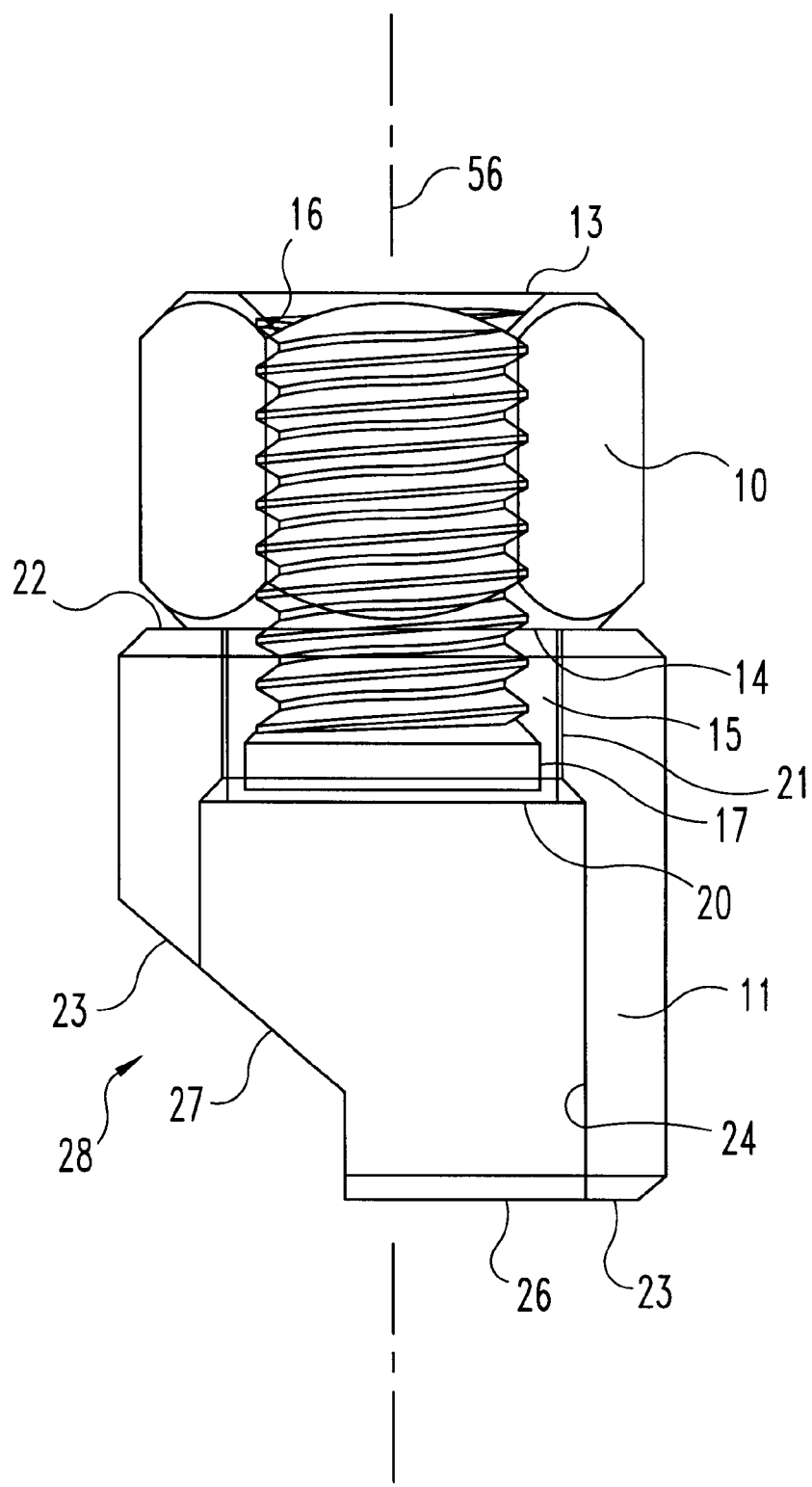
Figure 5:
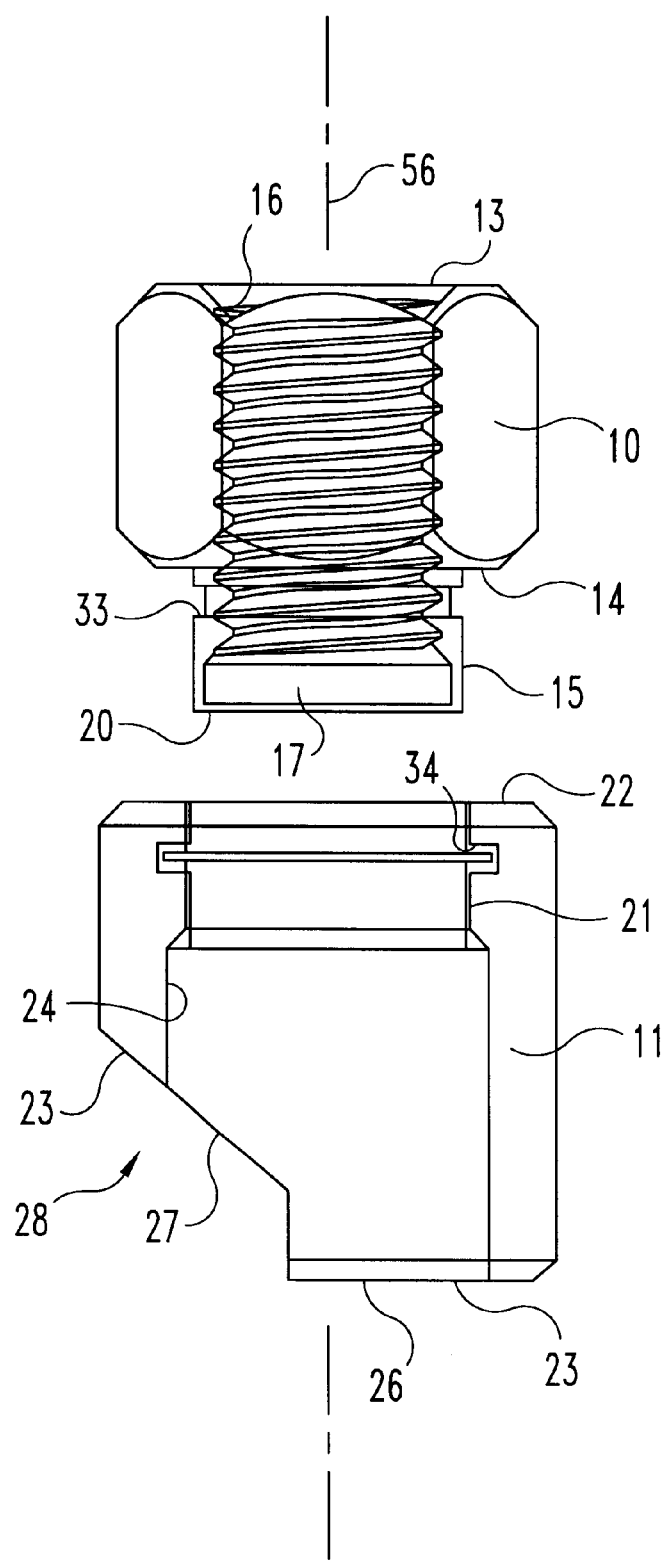

Details of nut 10 and clamp interface collar 11 are depicted in FIGS. 3 to 5. Nut 10 has an anterior face 13 and a posterior face 14, with posterior face 14 further including a male contact element 15 that is integrally connected to nut 10. Male contact element 15 is preferably round in cross-section with a flat posterior face 20. Thusly configured, male contact element 15 serves as a journal when male contact element 15 turns within the complementary female contact element 21 in clamp interface collar 11. Both nut 10 and male contact element 15 have a bore 17 down longitudinal axis 56 that opens onto the anterior face 13 of nut 10 and onto the posterior face of male contact element 15. Bore 17 includes a set of internal threads 16, and both bore 17 and threads 16 are sufficiently sized to accept machine threads 18, on the proximal portion 19 of reduction bolt 8 (FIGS. 1 & 2).

Clamp interface collar 11 has an anterior face 22 and a posterior face 23, with anterior face 22 further including a female contact element 21. Female contact element 21 is preferably round in cross-section and shaped to complement male contact element 15 on nut 10. Female contact element 21 serves as a race for male contact element 15 as nut 10 is turned about longitudinal axis 56. Clamp interface collar 11 has a bore 24 down longitudinal axis 56 that opens onto the anterior face 22 of clamp interface collar 11 and onto the posterior face 23 of clamp interface collar 11. Bore 24 is sufficiently sized to accept the passage of machine threads 18 and threadless region 25 (FIG. 2) on reduction bolt 18.

The posterior face 23 of clamp interface collar 11 is preferably shaped to complement the surface of clamp 7 or connection unit 7 against which clamp interface collar 11 is placed. In one embodiment, posterior face 23 includes a horizontal shoulder 26 and a non-horizontal edge 27 that partially defines the entrance of bore 24. Placed in this fashion, non-horizontal edge 27 cuts a notch 28 that opens into bore 24 from the longitudinal side of clamp interface collar 11. Non-horizontal edge 27 is sufficiently sized to accept the portion of lateral edge 29 of bolt interface washer 9 (FIG. 2) over which non-horizontal edge 27 is placed. And horizontal shoulder 26 is sufficiently sized to lide against the complementary horizontal surface 30 on connection unit 7 that surrounds aperture 46. In one preferred, horizontal shoulder 26 alone contacts connection unit 7, and non-horizontal edge 27 is sufficiently high on clamp interface collar 11 so as to provide a clearance 31 between bolt interface washer 9 on connection 7 and collar 11. In another preferred embodiment, horizontal shoulder 26 contacts connection unit 7 and non-horizontal edge 27 contacts bolt interface washer 9, and there is no clearance between bolt interface washer 9 and collar 11.

Given the previous description, there are at least two items that those of average skill in this art should recognize. Though male contact element 15 is shown contiguous to nut 10 and a female contact element 21 is placed within collar 11, one could exchange these locations, placing a female contact element within nut 10 and a male contact element on collar 11. Secondly, though female contact element 21 and male contact element 15 are shown with round cross-sections, one could also use other shapes, provided the resulting female-male engagement also allows nut 10 to rotate about longitudinal axis 56 in respect to collar 11.

Regarding other options and alterations, the practice of this invention may include additional structures. For example, referring to FIG. 1, one may include a window 32 in the longitudinal side of clamp interface collar 11. Or, referring to FIG. 5, one could provide male contact element 15 and female contact element 21 with annular grooves 33 and 34. One could then place a means to secure nut 10 and collar 11 within these grooves, such as snap ring 35. Then, when male contact element 15 is placed inside female contact element 21, snap ring 35 engages annular grooves 33 & 34 and thereby rotatably secures nut 10 to collar 11, nut 10 still being free to rotate in relation to collar 11 even though it is now attached to collar 11.

Details of reduction bolt 8 are best seen in FIG. 2. Reduction bolt 8 has a proximal portion 19 with machine threads 18, and a distal portion 36 with coarse threads 37. Coarse threads 37 have a thread convolution for engaging cancellous bone and terminate in a tapered tip 39. Tapered tip 39 helps to align reduction bolt 8 into a predrilled opening in a vertebra, and also allows coarse threads 37 to gradually engage and advance into the vertebra upon rotating reduction bolt 8. In this regard, although coarse threads are shown as a means to attach reduction bolt 8 to a vertebra, it is also contemplated that one could use a hook, mounted on the end of reduction bolt 8. Machine threads 18 are sized to accept the internal threads 16 of nut 10.

The distal end 39 of reduction bolt 8 includes a means for a driving tool to engage and twist bolt 8 into a vertebra. Reduction bolt 8 is shown with a six-sided socket 41 (FIG. 1) to mate with a screwdriver having a tip of a complementary configuration, however, other configurations could be also be used on distal end 39. For example, one could also use an external hex head configuration or a design that accepts a standard slotted screwdriver or a Phillips-headed screwdriver. Machine threads 18 preferably extend on the proximal portion 19 for a length that allows reduction bolt 8 to extend from the displaced vertebra 54, through connection unit 7 and collar 11, and into nut 10. Reduction bolt 8 is shown with a threadless region 25 between coarse threads 37 and machine threads 18. Threadless region 25, as well as the inside of aperture 46 in clamp 7, may be optionally roughened to increase friction between reduction bolt 8 and clamp 7, clamp 7 eventually being secured to the threadless region of reduction bolt 8.

The connection assembly or clamp 7, shown in FIGS. 1 and 2, is preferably a type with a rod connecting member 42 having an aperture 43 for receiving a portion of longitudinal member or spinal implant rod 2, as well as, a bolt connecting member 45 having an aperture 46 for receiving a portion of reduction bolt 8. Rod connecting member 42 and bolt connecting member 45 are preferably rotatably engaged to one another. A rod interface washer 47 is positioned over a portion of rod connecting member 42, and a bolt interface washer 9 is positioned over a portion of bolt connecting member 45. The rod interface washer 47 and the bolt interface washer 9 are then moveable in part between the rod connecting member 42 and the bolt connecting member 45. Interface washers 9 & 47 then have structure for engaging at least one of the longitudinal member 2 and rod connecting member 42, and for engaging at least one of the bolt 8 and the bolt connecting member 45, so as to prevent relative rotation of the longitudinal member 2 and the rod connecting member 42 and the bolt 8 and the bolt connecting member 45 when clamp 7 is tightened. Connection assembly 7 also includes structure 48 that may extend into either aperture 43 or 48 so as to urge longitudinal member 2 and reduction bolt 8 toward each other, and cause washers 9 and 47 to be pressed together between longitudinal member 2 and reduction bolt 8. In this regard, it should be noted that structure 48, such as the set-screw that is shown, could be fitted into any of threads 49, 50 or 51 to accomplish this result. Additional details of such a clamp can be found in U.S. Pat. Nos. 5,643,263 and 5,885,285 to Simonson, the disclosures of which are specifically incorporated into this specification by reference. Moreover, the commercial embodiment of this clamp is sold under the trademark TSRH-3D and is available from Medtronic Sofamor Danek, located in Memphis, Tenn. U.S.A.

In regard to additional options, it should be understood that clamp 7 need not include rod interface washer 47 in order to practice the present invention. As previously presented, clamp interface collar 11 includes notch 28 to accept the lateral face of bolt interface washer 9. Whether notch 28 is of sufficient size to also accept a second washer, such as rod interface washer 47, located between bolt interface washer 9 and aperture 43 is simply a matter of choice. Hence the present invention would contemplate an embodiment where either one or more interface washers are present between longitudinal member 2 and reduction bolt 8.

And as to clamps 5 & 6 (FIG. 1), it should be understood that these connection units can be any commercially available clamps that will appropriately anchor longitudinal member 2 to the vertebrae 52 & 53, which are adjacent the displaced vertebra 54. As shown, many surgeons may wish to use rod-to-bolt clamps 5 & 6 that similarly equipped with a bolt interface washer as clamp or connection 7 is equipped. But the use of such a connection to the non-displaced vertebrae is not necessary to the successful practice of the present invention. Hence, the present invention is not limited to any particular clamp that the practitioner may place on the non-displaced vertebrae 52 & 53.

Referring back to FIG. 1, an apparatus 1 for reducing the extent of displacement between adjacent vertebrae in a person's spinal column is shown. Although only one side of the spine is depicted for clarity, it should be understood that, in practice, the surgeon may routinely install the mirror image of apparatus 1 on the other side of the spinous processes 55. When apparatus 1 is to be installed, holes are formed in the displaced vertebra 54 and in the vertebrae on opposite sides of the displaced vertebra, 52 & 53. Vertebral anchors 3 & 4 and reduction bolt 8 are then respectively mounted in the holes in the vertebrae 52 & 53, and in the displaced vertebra 54. A longitudinal member 2, such as the spinal rod, is then positioned along the longitudinal axis of the spinal column, and firmly secured by any suitable clamp, here clamps 5 & 6, to vertebral anchors 3 & 4.

A third clamp or connection unit 7 is then placed loosely around reduction bolt 8 and longitudinal member 2. The third claim is of a design that engagement of a particular compression member simultaneously tightens both the longitudinal member 2 and reduction bolt 8 to the third clamp or connection unit 7. An example of such a clamp is commercially available from Medtronic Sofamor Danek, located in Memphis, Tenn. U.S.A. and is sold under the trademark TSRH-3D. With longitudinal member 2 residing in aperture 43 and reduction bolt 8 residing in aperture 46, a notched clamp interface collar 11 is slid over the machine threads 18 and rested on connection unit 7 with notch 28 positioned over the lateral side of bolt interface washer 9. Nut 10 is then preferably threaded over machine threads 18 by hand until nut 10 has made contact with collar 11, and the male contact element 15 of nut 10 is engaged with female contact element 21 of collar 11. Should nut 10 and collar 11 be rotatably attached, both nut 10 and collar 11 are lowered onto connection unit 7 as nut 10 is threaded onto reduction bolt 8. Thereafter, nut 10 is further tightened, typically with a wrench and socket, to pull displaced vertebra 54 toward longitudinal member 2 and into its proper position in alignment with vertebra 52 and 53. Should collar 11 contain the optional window 32, the surgeon can see when threadless region 25 enters collar 11, and use this information as an aid as to when displaced vertebra 54 has been placed in proper alignment. Once the displaced vertebra 54 is relocated back to its proper position, the compression member on connection unit 7 is engaged to fixedly secure reduction bolt 8 to longitudinal member 2. The surgeon then removes nut 10 and collar 11, and cuts away that proximal portion of reduction bolt 8 that extends proximally above connection unit 7.

While the invention has been illustrated and described in detail in the drawings and foregoing description, the same is to be considered as illustrative and not restrictive in character, it being understood that only the preferred embodiments have been shown and presented to the reader and that all changes and modifications that come within the spirit of the invention are desired to be protected.

We claim:

1. A reduction assembly for a spinal implant clamp that has a non-horizontal face, the spinal implant clamp being used to connect a bone bolt to a spinal implant rod, the reduction assembly comprising:

a reduction bolt, said reduction bolt having machine threads on a proximal portion and means for engaging a vertebra on a distal portion;

a nut, said nut operatively engaging the machine threads of said reduction bolt, said nut having a posterior face;

a collar, said collar having an opening for receiving a portion of said reduction bolt and for permitting translational movement of said collar over said reduction bolt; said collar having anterior and posterior faces, the anterior face of said collar and the posterior face of said nut having mutually engageable male and female contacts, said contacts adapted to allow said nut to rotate in respect to said collar.

2. The reduction assembly of claim 1, wherein the posterior face of said collar has a notch therein for receiving a portion of the non-horizontal face of a spinal implant clamp.

3. The reduction assembly of claim 2, wherein said notch partially defines the opening in the posterior face of said collar to pass said reduction bolt.

4. The reduction assembly of claim 1, wherein said collar has a window on a longitudinal side of said collar that opens between an inside and an outside of said collar.

5. The reduction assembly of claim 1, wherein said reduction bolt has a threadless region between the means for engaging and the machine threads.

6. The reduction assembly of claim 5, wherein said threadless region is roughened to increase friction between said reduction bolt and a spinal clamp.

7. The reduction assembly of claim 1, including means for rotatably connecting said nut to said collar.

8. An assembly for reducing a displaced vertebra and connecting the displaced vertebra to a spinal implant rod, comprising:

a reduction bolt, said reduction bolt having machine threads on a proximal portion and coarse threads on a distal portion;

a connection unit, said connection unit having a rod connecting portion with an opening for receiving a portion of the rod, and a bolt connecting portion having an opening for receiving a portion of said reduction bolt and for permitting translational movement of said connection unit over said reduction bolt;

at least one interface washer positioned over and between the rod connecting portion and the bolt connecting portion, said interface washer being moveable in part between the rod connecting portion and the bolt connecting portion, said interface washer having a lateral edge;

a nut, said nut operatively engaging the machine threads of said reduction bolt;

a collar, said collar having an opening for receiving a portion of said reduction bolt and for permitting translational movement of said collar over said reduction bolt; said collar having a posterior face, said collar having a notch in the posterior face for receiving a portion of the lateral edge of said interface washer, the notch partly defining the opening in the posterior face of said collar to pass said reduction bolt, said collar positioned on said reduction bolt, between said nut and said connection unit.

9. The assembly of claim 8, wherein said collar has a window in the longitudinal side of said collar to view said reduction bolt within said collar.

10. The assembly of claim 8, wherein said reduction bolt has a threadless region between the coarse threads and the machine threads.

11. The assembly of claim 10, wherein said threadless region is roughened and the walls of the opening for receiving a bolt in said connection unit is roughened to increase friction between said reduction bolt and said connection unit.

12. The assembly of claim 8, wherein said nut has a posterior face, said collar has an anterior face, and the anterior face of said collar and the posterior face of said nut have mutually engageable male and female contacts, and wherein said contacts are adapted to allow said nut to rotate in respect to said collar.

13. The assembly of claim 12, including a snap ring operably connecting said collar and said nut.

14. The assembly of claim 8, wherein the rod connecting portion and the bolt connecting portion of said connection unit are rotatably engaged to each other, and including means extendable into the opening of at least one of the rod connecting portion and the bolt connecting portion, for urging one of the rod and the bolt toward the other, causing said interface washer to operatively engage the rod and the bolt against rotation relative to said interface washer, preventing rotation of the rod and the rod connecting portion relative to the bolt and the bolt connecting portion, and securing the rod to the bolt.

15. An apparatus for use in reducing a displaced vertebra, comprising:

a longitudinal member positionable along the longitudinal axis of the spine;

a first vertebral anchor and a second vertebral anchor;

a first clamp, a second clamp, and a third clamp, said first clamp fixedly securing said first vertebral anchor to said longitudinal member, said second clamp fixedly securing said second vertebral anchor to said longitudinal member, said third clamp having a longitudinal member connecting portion with an opening for receiving a portion of the longitudinal member, and a bolt connecting portion having an opening for receiving a portion of a reduction bolt and for permitting translational movement of said third clamp over a reduction bolt;

a reduction bolt, said reduction bolt positioned inside the bolt connecting portion of said third clamp, said reduction bolt having machine threads on a proximal portion and coarse threads on a distal portion;

a bolt interface washer, said bolt interface washer positioned over and between the longitudinal member connecting portion and the bolt connecting portion of said third clamp, said interface washer being moveable in part between the longitudinal connecting portion and the bolt connecting portion, said bolt interface washer having a lateral edge;

a nut, said nut threadably engaged to the machine threads on the proximal portion of said bolt;

a clamp interface collar, said clamp interface collar having an opening for receiving a portion of said reduction bolt and for permitting translational movement of said collar over said reduction bolt; said clamp interface collar having a notch therein for receiving a portion of the lateral edge of said bolt interface washer, said clamp interface collar positioned on said reduction bolt, between said nut and said third clamp;

whereby said nut can be tightened against said clamp interface collar to pull said reduction bolt and thereby move a displaced vertebra toward the longitudinal member, said third clamp can be tightened to fixedly secure said reduction bolt to said longitudinal member, and said nut and said clamp interface collar can be removed from the patient without the vertebra moving away from said longitudinal member.

16. The assembly of claim 15, wherein the longitudinal member connecting portion and the bolt connecting portion of said connection unit are rotatably engaged to each other.

17. The assembly of claim 16, wherein said third clamp includes means extendable into the opening of at least one of the longitudinal member connecting portion and the bolt connecting portion, for urging one of the longitudinal member and the reduction bolt toward the other, causing said interface washer to operatively engage the rod and the bolt against rotation relative to said interface washer, and securing the longitudinal member to the bolt.

18. The assembly of claim 15, wherein the longitudinal side of said clamp interface collar has a window that opens between the interior and the exterior of said clamp interface collar whereby a surgeon may view said reduction bolt within said clamp interface collar.

19. The assembly of claim 15, wherein said reduction bolt has a threadless region between the coarse threads and the machine threads.

20. The assembly of claim 19, wherein said threadless region is roughened to increase friction between said reduction bolt and said third clamp.

21. The assembly of claim 15, wherein said nut has a posterior face, said clamp interface collar has an anterior face, and the anterior face of said collar and the posterior face of said nut have mutually engageable male and female contacts, and wherein said contacts are adapted to allow said nut to rotate in respect to said collar.

22. The assembly of claim 21, including means for operably connecting said male and female contacts.

23. A method for aligning a displaced vertebra, comprising the steps of:

attaching a bone bolt to a displaced vertebra, said bone bolt having coarse threads to engage the vertebra on one portion of the bolt and machine threads on a second portion of the bone bolt;

positioning a spinal rod along the longitudinal axis of the spine;

positioning a clamping device on the bone bolt and the spinal rod, said clamping device having a compression member that, when engaged, simultaneously tightens the bone bolt and the spinal rod to the clamping device;

sliding a collar over the bone bolt and allowing the collar to rest against the clamping device;

threading a nut over the machine threads on the bone bolt and against the collar and thereby pull the bone bolt through the collar and the clamping device and move the displaced vertebra toward the spinal rod;

tightening the compression member on the clamping device to hold the bone bolt and the spinal rod; and removing the nut and collar from the bone bolt.

24. The method of claim 23, including the step of cutting the bone bolt adjacent the clamping device.

\* \* \* \* \*